(12) United States Patent
Ji et al.

(10) Patent No.: US 11,216,683 B2
(45) Date of Patent: Jan. 4, 2022

(54) COMPUTER AIDED SCANNING METHOD FOR MEDICAL DEVICE, MEDICAL DEVICE, AND READABLE STORAGE MEDIUM

(71) Applicant: General Electric Company, Schenectady, NY (US)

(72) Inventors: Yongnan Ji, Beijing (CN); Bo Guo, Beijing (CN); Shiyu Li, Beijing (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/455,977

(22) Filed: Jun. 28, 2019

(65) Prior Publication Data
US 2020/0311456 A1 Oct. 1, 2020

(51) Int. Cl.
| | | |
|---|---|---|
| G06K 9/32 | (2006.01) | |
| G06T 7/00 | (2017.01) | |
| G16H 30/20 | (2018.01) | |
| G16H 30/40 | (2018.01) | |
| G06K 9/62 | (2006.01) | |
| G06T 7/60 | (2017.01) | |

(52) U.S. Cl.
CPC ......... *G06K 9/3241* (2013.01); *G06K 9/6256* (2013.01); *G06T 7/0012* (2013.01); *G06T 7/60* (2013.01); *G16H 30/20* (2018.01); *G16H 30/40* (2018.01); *G06K 2209/05* (2013.01); *G06T 2207/10024* (2013.01); *G06T 2207/20081* (2013.01); *G06T 2207/20084* (2013.01)

(58) Field of Classification Search
USPC .............................. 382/128, 131, 155–156
See application file for complete search history.

(56) References Cited

U.S. PATENT DOCUMENTS

| | | | | |
|---|---|---|---|---|
| 6,999,549 | B2 * | 2/2006 | Sabol ................... | A61B 5/4872 378/5 |
| 7,072,435 | B2 * | 7/2006 | Metz ..................... | A61B 6/032 378/62 |
| 8,693,760 | B2 * | 4/2014 | Yokosawa .......... | G01R 33/4833 382/131 |
| 9,805,470 | B2 * | 10/2017 | Bhatia ...................... | G06T 5/00 |
| 10,852,379 | B2 * | 12/2020 | Chen .................. | G01R 33/4818 |
| 2006/0100518 | A1 * | 5/2006 | Krishnan ................. | A61B 8/08 600/450 |
| 2009/0124903 | A1 * | 5/2009 | Osaka .................... | A61B 8/485 600/443 |

(Continued)

*Primary Examiner* — Ishrat I Sherali

(57) ABSTRACT

A computer aided scanning method for a medical device is provided in the present invention, comprising step 1: recognizing and analyzing a pre-scan image through a pre-trained neural network to determine and identify a region of interest in the pre-scan image; and step 2: determining, according to feature information of the identified region of interest, scanning parameters for further scanning of the region of interest. A medical device employing the above method and a computer readable storage medium for performing the method are further provided in the present invention. The method, the medical device, and the readable storage medium provided by the present invention can automatically identify a region of interest, determine a corresponding auxiliary line and subsequent scanning parameters, and improve the scanning efficiency and accuracy of the medical device.

7 Claims, 9 Drawing Sheets

Recognize and analyze a pre-scan image through a pre-trained neural network to determine and identify a region of interest in the pre-scan image — S1

Determine, according to feature information of the identified region of interest, scanning parameters for further scanning of the region of interest — S2

(56) References Cited

U.S. PATENT DOCUMENTS

| | | | |
|---|---|---|---|
| 2013/0105699 A1* | 5/2013 | Asma | A61B 6/488 250/363.03 |
| 2015/0269718 A1* | 9/2015 | Bhatia | G06K 9/46 382/128 |
| 2018/0218516 A1* | 8/2018 | Reda | G06T 7/70 |
| 2019/0377047 A1* | 12/2019 | Chen | G01R 33/4818 |
| 2020/0311456 A1* | 10/2020 | Ji | G06K 9/6256 |
| 2020/0320326 A1* | 10/2020 | Dou | G06N 3/08 |
| 2020/0365267 A1* | 11/2020 | Lauer | G16H 50/20 |
| 2021/0080531 A1* | 3/2021 | Gui | G01R 33/543 |

\* cited by examiner

COMPUTER AIDED SCANNING METHOD FOR MEDICAL DEVICE, MEDICAL DEVICE, AND READABLE STORAGE MEDIUM

CROSS REFERENCE TO RELATED APPLICATIONS

This application claims the benefit of Chinese Patent Application No. 201810697149.8 filed on Jun. 29, 2018, the disclosure of which is herein incorporated by reference in its entirety.

TECHNICAL FIELD

The present invention relates to the field of medical imaging, and in particular, to a computer aided scanning method for a medical device, a medical device using the method, and a computer readable storage medium for performing the method.

BACKGROUND

During the use of medical imaging devices such as magnetic resonance tomography (MRT), computer resonance tomography (CT), X-ray, ultrasound, and radiotherapy, a physician first needs to scan a patient to obtain a pre-scan image, and then the physician needs to select a region of interest manually and determine a scanning position and other scanning parameters. However, the accuracy of manually selecting a region of interest is limited by the physician's personal experience and habits. In addition, the manual selection is time consuming, and will in turn increase the time of the entire scanning process.

Therefore, it is necessary to provide a new computer aided scanning method for a medical device that can automatically identify a region of interest and determine corresponding scanning parameters to improve scanning efficiency and accuracy.

SUMMARY

Other features and aspects will be clear through the following detailed descriptions, accompanying drawings, and claims.

A computer aided scanning method for a medical device is provided in the present invention, comprising: step 1: recognizing and analyzing a pre-scan image through a pre-trained neural network to determine and identify a region of interest in the pre-scan image; and step 2: determining, according to feature information of the identified region of interest, scanning parameters for further scanning of the region of interest.

Preferably, in the step 2, the scanning parameters for further scanning of the region of interest are determined by determining an auxiliary line in the pre-scan image.

Preferably, the neural network is trained by the following steps: capturing a plurality of pre-scan images to obtain a pre-scan image set;

marking regions of interest on the pre-scan images to obtain a training set; and training a neural network by using the pre-scan image set as an input and the training set as an output to obtain the pre-trained neural network.

Preferably, before the step 1, the method further comprises: converting the pre-scan image acquired when pre-scanning of the medical device is performed into a pre-scan image in a red, green, and blue (RGB) format, and in the step 1, the pre-trained neural network recognizes and analyzes the pre-scan image in the red, green, and blue (RGB) format, and outputs a binary image having the identified region of interest.

Preferably, the step 2 further comprises: determining a feature point in the identified region of interest, and determining the auxiliary line based on at least two of the feature points.

Preferably, the feature point comprises a geometric center point of the identified region of interest, and the auxiliary line is determined by drawing a perpendicular line based on two adjacent geometric center points.

Preferably, the feature point comprises a vertex of the identified region of interest, and the auxiliary line is determined by fitting a straight line based on two adjacent groups of vertexes.

A medical device is provided in another aspect of the present invention, comprising:

a scanning portion, configured to capture a pre-scan image; and a computing portion, comprising:

a pre-trained neural network, wherein the pre-trained neural network is configured to recognize and analyze the pre-scan image to determine and identify a region of interest in the pre-scan image; and the computing portion is configured to determine, according to feature information of the identified region of interest, scanning parameters for further scanning of the region of interest.

Preferably, the computing portion is configured to determine the scanning parameters for further scanning of the region of interest by determining an auxiliary line in the pre-scan image.

Preferably, the computing portion further comprises a pre-processing portion, configured to convert the pre-scan image acquired when pre-scanning of the medical device is performed into a pre-scan image in a red, green, and blue (RGB) format, and the pre-trained neural network recognizes and analyzes the pre-scan image in the red, green, and blue (RGB) format, and outputs a binary image having the identified region of interest.

Preferably, the computing portion is configured to determine a feature point in the identified region of interest, and determine the auxiliary line based on at least two of the feature points.

Preferably, the computing portion is configured to determine a geometric center point of the identified region of interest as the feature point, and determine the auxiliary line by drawing a perpendicular line based on two adjacent geometric center points.

Preferably, the computing portion is configured to determine a vertex of the identified region of interest, and determine the auxiliary line by fitting a straight line based on two adjacent groups of vertexes.

A computer readable storage medium storing an instruction is further provided in another aspect of the present invention, wherein when executed by a processor, the instruction implements the steps of the method of any of claims 1 to 7.

BRIEF DESCRIPTION OF THE DRAWINGS

The present invention may be better understood by describing exemplary embodiments of the present invention with reference to accompanying drawings, in which.

DETAILED DESCRIPTION

Figure 1:
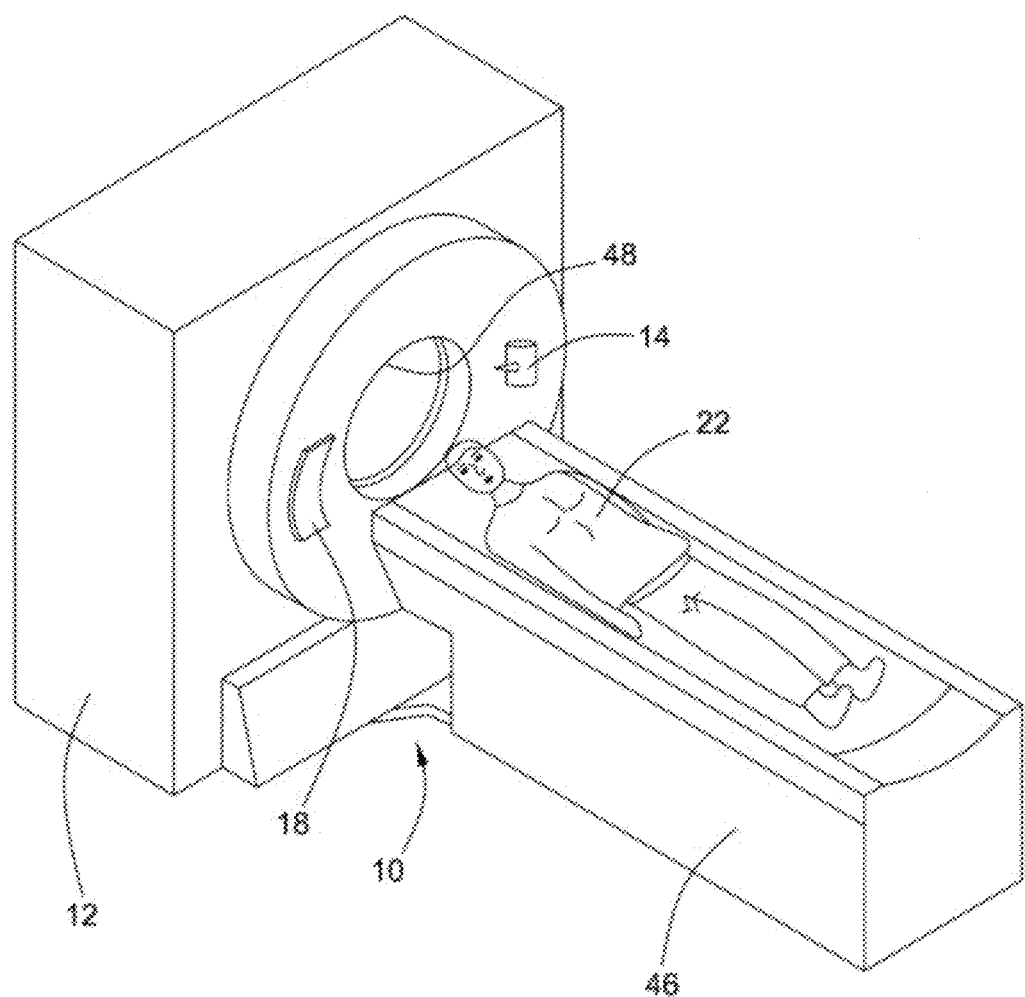
FIG. 1 is a schematic diagram of a medical device according to an embodiment of the present invention.

Specific implementations of the present invention will be described in the following. It should be noted that during the specific description of the implementations, it is impossible to describe all features of the actual implementations in detail in this specification for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another. Moreover, it can also be understood that although the efforts made in such development process may be complex and lengthy, for those of ordinary skill in the art related to the disclosure in the present invention, some changes in design, manufacturing, production, or the like based on the technical content disclosed in this disclosure are only conventional technical means, and should not be construed as that the content of this disclosure is insufficient.

Unless otherwise defined, technical terms or scientific terms used in the claims and the description should be construed in the ordinary meanings that can be understood by those of ordinary skill in the art of the present invention. The words "first," "second", and similar words used in the description and claims of the present application for invention do not denote any order, quantity, or importance, but are merely used to distinguish different components. The word "one," "a/an," or a similar word does not indicate a quantity limitation, but means that there is at least one. The word "include," "comprise," or a similar word is intended to mean that a component or an object that appears before the word "include" or "comprise" encompasses a component or an object and equivalent components that are listed after the word "include" or "comprise," and does not exclude other components or objects. The word "connect," "connected," or a similar word is not limited to a physical or mechanical connection, and is not limited to a direct or indirect connection.

In the following description, numerous specific details are set forth, such as examples of specific components, devices, and methods, thus providing a thorough understanding of the embodiments of the present invention. However, it will be apparent to those skilled in the art that it is unnecessary to implement the embodiments of the present invention by using these specific details. In other cases, well-known materials or methods are not described in detail to avoid unnecessarily obscuring the embodiments of the present invention. Although the present invention may have various modifications and alternatives, specific embodiments and methods thereof are shown as examples in the accompanying drawings and described in detail herein. However, it should be understood that the present invention is not intended to be limited to the disclosed specific form. In contrast, the present invention will cover all modifications, equivalents, and replacements falling within the spirit and scope of the present invention.

Unless otherwise specified, as will be apparent from the discussion below, it will be appreciated that terms such as "segmentation", "generation", "registration", "determination", "alignment", "positioning", "processing", "calculation", "selection," "estimation," "detection," and "tracking" may refer to actions and processes of a reference computer system or similar electronic computing device, which manipulates data represented as a physical (e.g., electronic) quantity in a register and a memory of the computer system, and transforms the data into other data similarly represented as a physical quantity in the memory or register of the computer system or in a device for storing, transmitting, or displaying such type of information. The embodiments of the method described in this text may be implemented using computer software. If written in a programming language that conforms to recognized criteria, a sequence of instructions designed to implement the method can be compiled for execution on a variety of hardware platforms and for interfacing to a variety of operating systems. In addition, the embodiments of the present invention have not been described with reference to any particular programming language. It will be appreciated that the embodiments in the present invention can be implemented using a variety of programming languages.

A new medical device and a computer aided scanning method thereof are provided in the present invention, which can automatically identify a region of interest in a pre-scan image and determine an auxiliary line, so as to enable quick and accurate determination of scanning parameters for subsequent scanning, thus improving scanning efficiency and accuracy.

During scanning of a medical device, a physician needs to set different scanning parameters for particular scan sites. Using computer tomography (CT) as an example, for different regions of interest (ROI), parameters thereof include at least a scanning angle, a scanning dose, a scanning layer thickness, and other scanning parameters. Therefore, a pre-scan image, also referred to as a scout scan, is usually captured before actual scanning. That is, a bulb tube inside the CT scan device is fixed at an angle to capture a pre-scan image of a patient. Similarly, an imaging device such as a magnetic resonance imaging device, an X-ray radiographic device, and a radiotherapy device also has a similar pre-scanning operation to facilitate subsequent further scanning.

Figure 2:
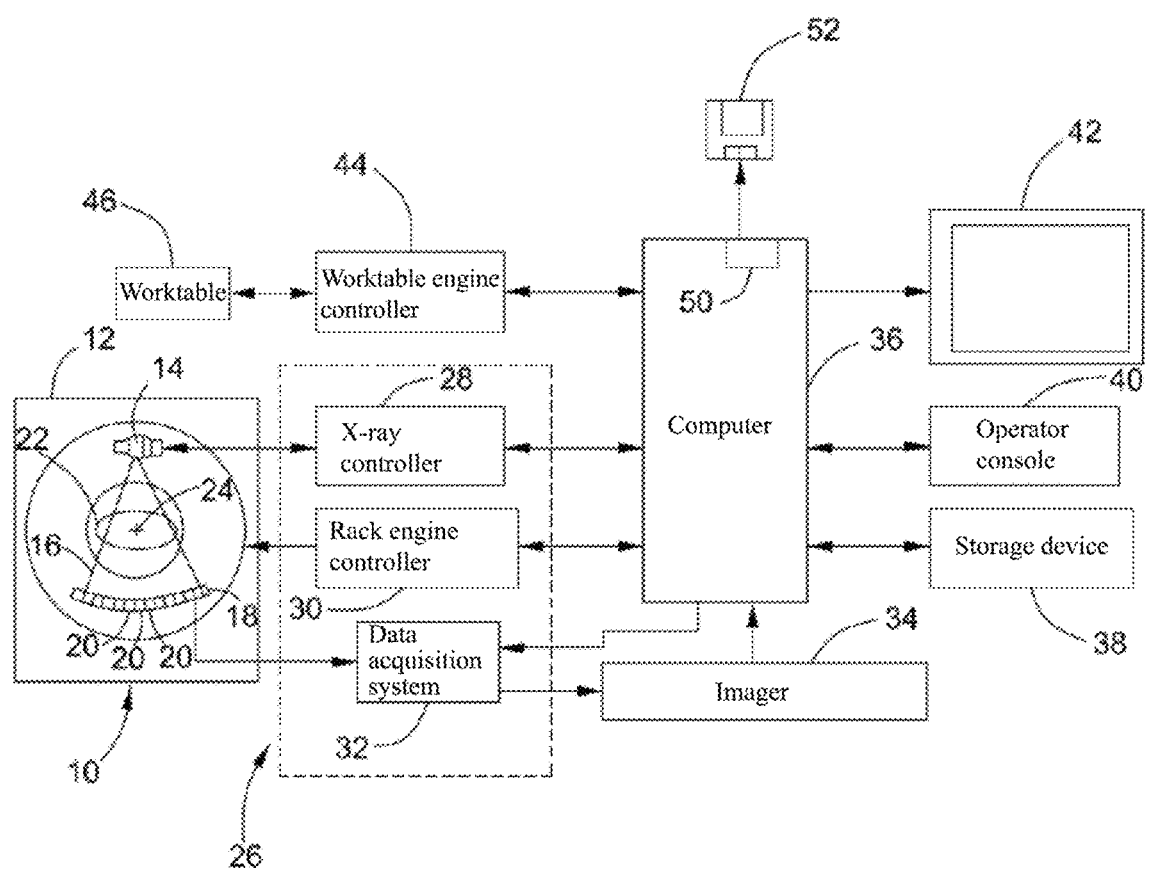
FIG. 2 is a modular block diagram of a medical device according to an embodiment of the present invention.

Specifically, using CT as an example, FIG. 1 is a schematic diagram of a CT system 10. FIG. 2 is a schematic block diagram of the system 10 shown in FIG. 1. In the exemplary embodiment, the CT system 10 includes a scanning portion 12. The scanning portion 12 includes a rack and a ray source 14 disposed thereon and configured to emit X-ray beams 16 to a detector 18 located on the other side.

The detector array 18 includes a number of detector rows (not shown). The detector rows include a plurality of detection components 20 and is configured to sense X-ray beams transmitted through a patient 22. The detection component 20 is configured to generate an electrical signal representative of the density of collisional radiation beams. The electrical signal representative of the density of the collisional radiation beams can represent the degree of attenuation of the X-ray beams after passing through the patient. During the scanning to acquire ray projection data, the rack and the components mounted thereon can rotate about a rotation center 24. FIG. 2 shows only one row of detection components 20 (i.e., a detector row). However, the detector 18 may include a number of parallel detector rows consisting of detection components 20, such that projection data corresponding to a plurality of parallel layers or quasi-parallel layers can be obtained simultaneously by one scan.

The rotation of the rack and the operation of the ray source 14 are controlled and managed by a control apparatus 26 of the CT system 10. The control apparatus 26 includes a ray controller 28 that supplies energy and timing signals to the ray source 14 and a rack engine controller 30 that controls the rotational speed and the position of the rack. A data acquisition system 32 in the control apparatus 26 samples analog data from the detection components 20 and converts the analog data into digital signals for subsequent processing. An image reconstructor 34 receives the sampled and digitized ray data from the data acquisition system 32 for high speed image reconstruction. The reconstructed image is input to a computing portion 36, and the computing portion 36 stores the image in a storage device 38. The computing portion 36 includes a processor or central processing unit (CPU) coupled, through an input/output interface, to one or a plurality of non-transitory computer readable media (e.g., a computer storage or a memory), an output device (e.g., a monitor, a display, a printer, etc.), and various input devices (e.g., a mouse, a keyboard, a touchpad, a voice recognition module, etc.). Preferably, the computing portion may be provided with a graphics controller chip such as a graphics processing unit (GPU) supporting high performance graphics functions. In some application scenarios, the computing portion may also be a workstation or even a distributed cloud computing system.

The computing portion 36 receives instructions and scanning parameters input through an operator control panel 40 that includes a keyboard and(or) other user input apparatuses. Through a display apparatus 42, an operator can observe data related to a scanning process at different stages of the scanning process, such as the pre-scan image described above or other reconstructed images. The computing portion 36 uses the instructions and parameters provided by the operator to provide control signals and associated data to the data acquisition system 32, the ray controller 28, and the rack engine controller 30. In addition, the computing portion 36 operates a worktable engine controller 44 to control a motorized scanning bed 46 configured to place the patient 22 into the rack 12. In particular, the scanning bed 46 moves the position of the patient 22 through an opening 48 of the rack.

Figure 3:
FIG. 3 is a schematic diagram of a pre-scan image according to an embodiment of the present invention.
Figure 4:
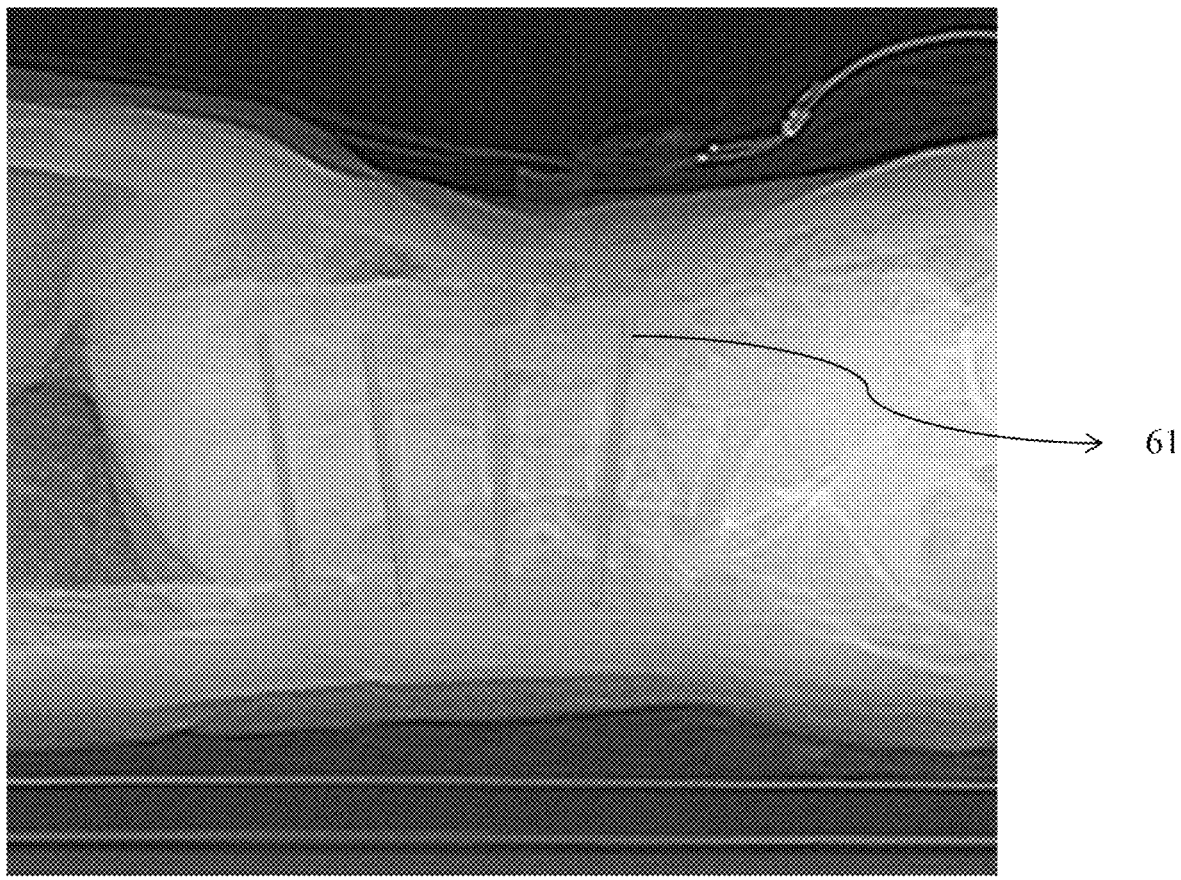
FIG. 4 is a schematic diagram of a scan auxiliary line of a pre-scan image according to an embodiment of the present invention.
Figure 5:
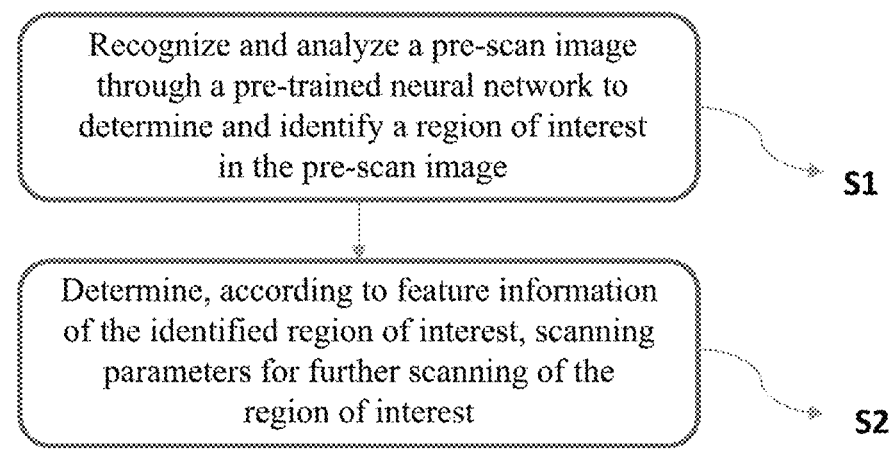
FIG. 5 is a flowchart of a computer aided CT scanning method according to an embodiment of the present invention.

During actual operation, the patient lies on the scanning bed 46, and a lateral scout scan, i.e., a pre-scan image, is captured on the waist of the patient. The lateral scout scan of the waist as shown in FIG. 3 is obtained by the image reconstructor 34, and is displayed on the display apparatus 42. In a conventional scanning process, the operator, e.g., the physician, manually determines scanning parameters such as a scanning angle for subsequent formal scanning in the displayed scout scan by the user input apparatus according to his/her own experience after observing the pre-scan image. Specifically, assuming that the scout scan of the waist in FIG. 3 is used for setting scanning angles for intervertebral disc spaces, each lumbar vertebra is a region of interest, and the physician draws an auxiliary line 61, as shown in FIG. 4, between every two lumbar vertebrae manually according to his/her own experience and judgment on the position of each lumbar vertebra shown in FIG. 3.

In the subsequent formal scanning, the CT scan device performs scanning and image reconstruction according to parameter limits such as the position, the angle, and the like of the auxiliary line. Throughout the process, the personal judgment of the physician plays a decisive role. At the same time, the human participation in determination of the auxiliary line increases the time of the entire scan, and the human factor will affect the accuracy of the subsequent scanning.

In one embodiment, the computing portion 36 includes a machine readable medium 52, such as an apparatus that reads instructions or data from a floppy disk, a compact disc (CD-ROM), or a digital versatile disc (DVD), e.g., a floppy disk drive, a CD-ROM drive, or an optical disc drive. It should be understood that there also exist other suitable types of machine readable memories (such as a rewritable compact disc and a flash memory), and none of them is excluded herein. In another embodiment, the computing portion 36 executes instructions stored in firmware (not shown). In general, at least one processing unit installed in the data acquisition system 32, the image reconstructor 34, and the computing portion 36 as shown in FIG. 2 is programmed with a program that performs the following method steps. However, the methods described below are not limited to the CT system 10 but can be used in conjunction with other different types of imaging systems mentioned above.

The computing portion is programmed to be capable of performing a computer aided method for scanning and imaging a patient, thus alleviating the above-mentioned problem of low scanning efficiency caused by manual setting of the scanning parameters, and details will be described herein below.

Figure 6:
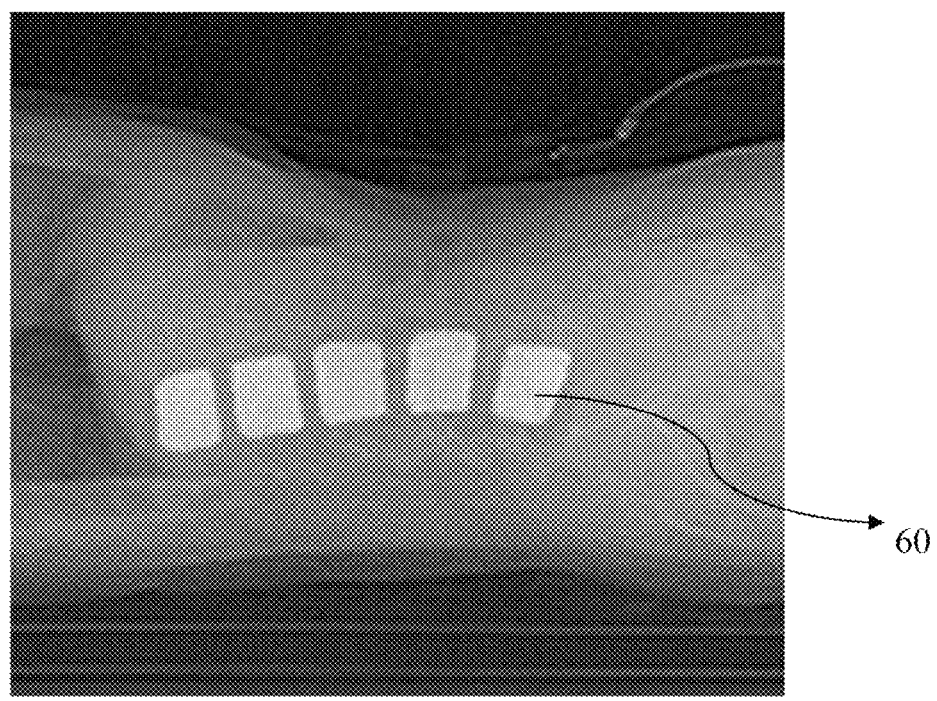
FIG. 6 is a schematic diagram of an image having the identified region of interest according to an embodiment of the present invention.

FIG. 6 is a flowchart of a computer aided scanning method for a medical device according to an embodiment of the present invention. As can be understood by those skilled in the art, other types of medical devices, such as a magnetic resonance imaging device, an X-ray radiographic device, and an ultrasonic device, can apply the scanning method provided by the present invention, and the scanning accuracy and speed can further be improved. After a patient lies on a scanning bed and is prepared, the medical device performs pre-scanning to obtain a pre-scan image. The pre-scan image includes a region of interest (ROI), for example, a region of any organ of interest to a physician such the lumbar vertebra, the spine, and the lungs.

In step S1, the pre-scan image is recognized and analyzed by a pre-trained neural network to determine and identify one or a plurality of regions of interest in the pre-scan image. In some embodiments, the pre-scan image needs to be pre-processed before being input to the neural network, and the pre-processing includes image noise reduction, filtering, normalization, and the like. It should be understood by those skilled in the art that a neural network (NN), also referred to as an artificial neural network (ANN), is a mathematical or computational model that mimics the structure and functions of a biological neural network, for estimating or approximating functions. The neural network performs computing by a large number of artificial neuronal connections. In most cases, the artificial neural network can change the internal structure based on external information, and is a self-adaptive system.

It should be noted that there are many types of neural networks, such as a full convolutional neural network and a perceptron neural network. In the embodiment of the present invention, the pre-scan image can be recognized by any one or a plurality of the above neural networks. Only some of the neural networks are recorded in the file of this application. It should be understood that various neural networks generated based on the neural network principle and algorithms derived therefrom all fall within the protection scope of the present invention. The specific training method of the neural network is described in detail in the subsequent sections. The pre-trained neural network employed in the present invention will identify an image of the region of interest. Assuming that the region of interest includes lumbar vertebrae, and the trained neural network identifies lumbar vertebrae 60, as specifically shown in FIG. 6.

The recognition and analysis speed of the neural network is very fast, and the result can be output within 1 second. As proved by experimenting on a plurality of pre-scan images, the trained neural network provided by the present invention can achieve the accuracy of more than 95%. The trained neural network model and associated computational algorithms of the computing portion are compiled as computer programs and stored in a computer readable medium. The computer readable medium includes a random access memory (RAM), a read only memory (ROM), a magnetic floppy disk, a flash memory, and other types of memories, or a combination thereof. The computer readable program code is executed by a central processing unit (CPU) or graphics processing unit (GPU) of the computing portion for control and/or processing.

In step S2, parameters for further scanning of the region of interest are determined according to feature information of the identified region of interest. In some embodiments, an auxiliary line is determined based on the feature information of the identified region of interest, and the auxiliary line is used to determine parameters for further scanning, such as a scanning angle and a scanning position. In practical applications, the region of interest recognized and analyzed by the neural network is usually an organ or tissue whose contour has a specific shape. In this embodiment, the computing portion can recognize the feature information based on the shape, and determine the auxiliary line according to the feature information. For the image of the lumbar vertebrae 60 having the identified region of interest as shown in FIG. 6, the computing portion may determine the geometric center point of each lumbar vertebra, a connection line is drawn between two adjacent geometric center points, and then a perpendicular line, preferably a midperpendicular line, is drawn. The auxiliary line can be determined with reference to the midperpendicular line, thereby determining a subsequent scanning angle. A scanning layer thickness can also be obtained by drawing a perpendicular line on the connection line between the geometric center points in a similar manner. Similarly, a corresponding scanning auxiliary line can be obtained by respectively drawing a midperpendicular line for every two adjacent geometric center points.

Figure 7:
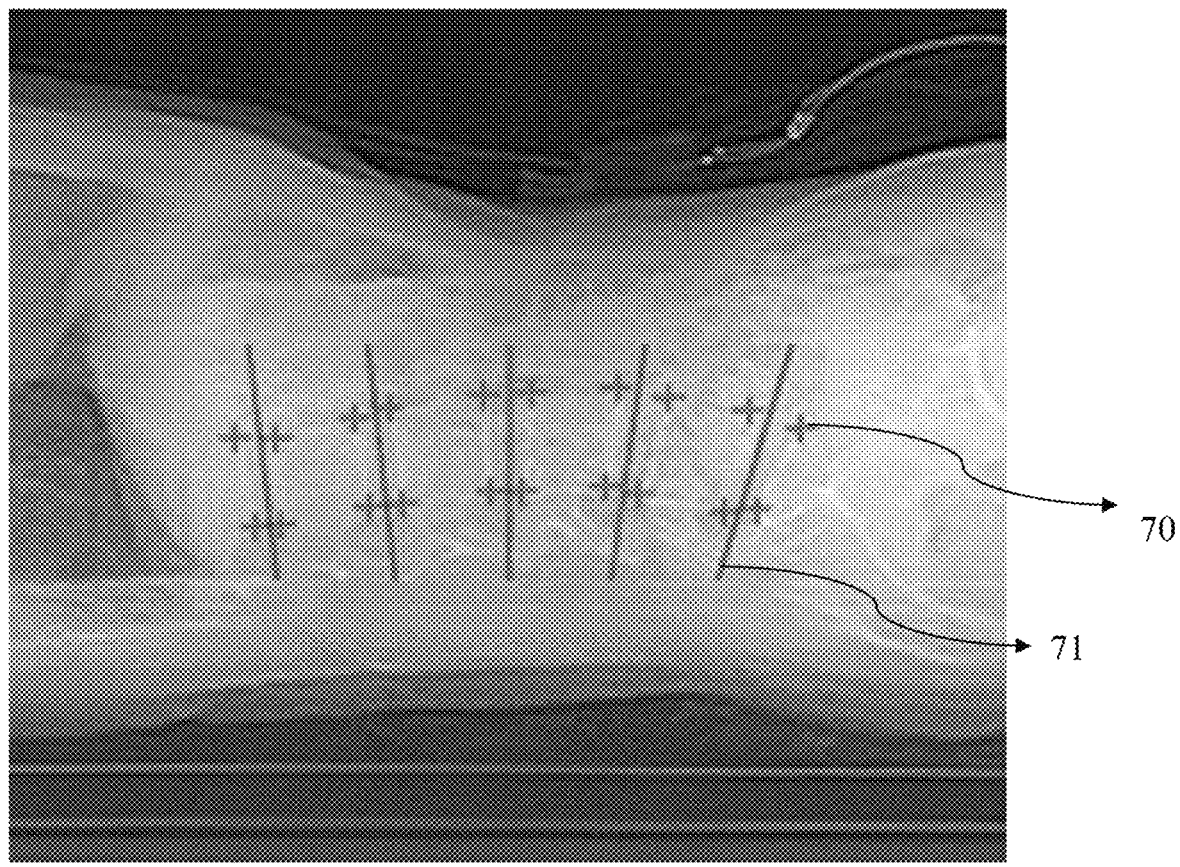
FIG. 7 is a schematic diagram of a scan auxiliary line of a pre-scan image according to an embodiment of the present invention.

It can be understood by those skilled in the art that there may be more than two feature points acquired based on the region of interest, and the positions of the feature points are not limited to the geometric center points. As shown in FIG. 7, according to the identified graphic information of the lumbar vertebrae, four vertices 70 of each lumbar vertebra are used as feature points, and an algorithm for identifying the vertices of a polygon is not described again. Two groups of adjacent feature points between adjacent lumbar vertebrae are shown. A straight line 71 is obtained by fitting based on the two groups of adjacent feature points, that is, the four vertices 70, so that distances from the fitted straight line 71 to the four identification points are as equal as possible, and the scanning auxiliary line can be determined based on the fitted straight line 71. Analogously, other auxiliary lines can be obtained by performing the same calculation method for two adjacent lumbar vertebrae, thereby determining the subsequent scanning angle.

The auxiliary line determined by the above method can achieve speed and accuracy that cannot be achieved by manual selection. After the auxiliary line is obtained, the display apparatus of the medical device can display the scan auxiliary line, and subsequent scanning operations are performed according to the scanning auxiliary line, thus obtaining an image of the region of interest. In some application scenarios, the physician will confirm or fine-tune the scanning auxiliary line to further improve the accuracy of the scanning auxiliary line.

Figure 8:
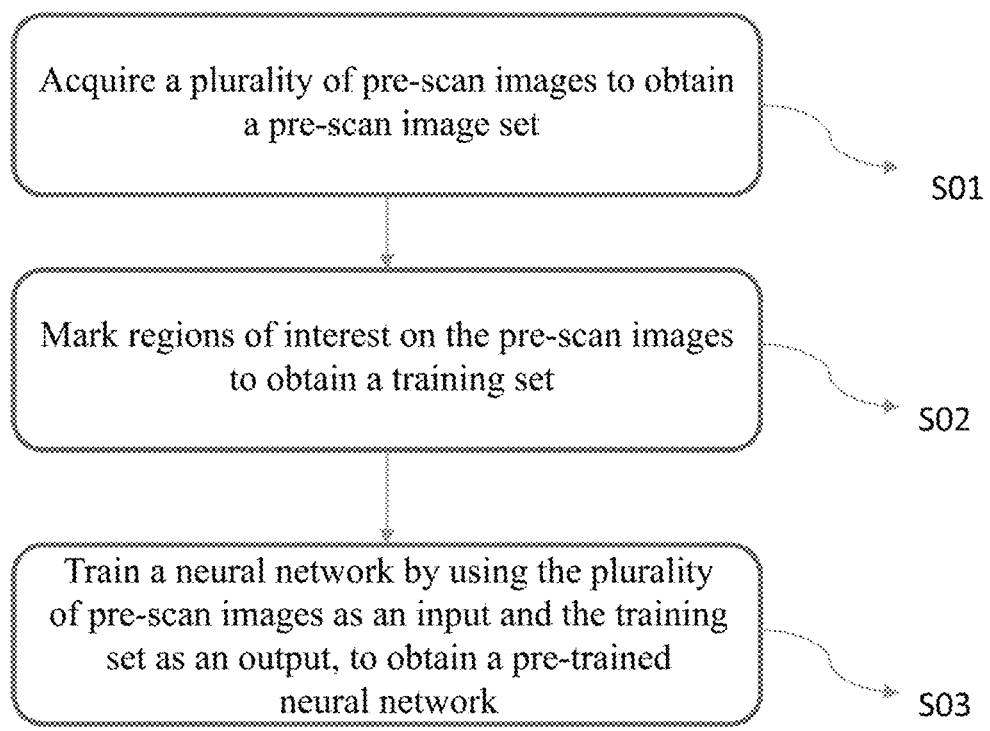
FIG. 8 is a flowchart of pre-training of a pre-trained neural network according to an embodiment of the present invention.

Specifically, a neural network needs to be pre-trained before the aforementioned medical device acquires the pre-scan image. A flowchart of pre-training the pre-trained neural network is shown in FIG. 8. The so-called pre-training the neural network is inputting enough samples to the neural network, and adjusting the structure of the network (for example, adjusting weights) by a certain algorithm, so that the output of the network is consistent with an expected value. The step of pre-training the neural network can be performed in the development and design phase of the medical device, and includes the following steps.

First, for a certain type of medical device, such as an X-ray photography device, in step S01, a plurality of pre-scan images are acquired, wherein the pre-scan images need to include regions of interest, and a set of pre-scan images is obtained. The pre-scan images may be a plurality of pre-scan images from one person or from different persons, may be from the same model of medical device, or may be from different models of medical devices having different image resolutions. The set of different pre-scan images needs to be normalized first.

In step S02, the regions of interest on the pre-scan images are marked. For example, grayscale values of the regions of interest on the pre-scan images are uniformly set to a maximum value or a minimum value, as long as they can be distinguished from other pixel points. The marked regions of interest may be regions of interest manually determined by the physician, or may be regions of interest recognized by an automated recognition method. The set of pre-scan images marked with the regions of interest is used as a training set.

The pre-scan images, in one-to-one correspondence with the pre-scan images marked with the regions of interest, are used as a group of sample data for training. Theoretically, the larger amount of training sample data, the better. Each neural network has its own requirement on the number of trained samples, and the number of samples should be enough for training so that the output of the neural network matches an expected value. Specifically, for pre-scan images of the medical device, a sample size of at least a few thousands of or more images is required.

In step S03, the neural network is trained by using the set of pre-scan images as an input of the neural network and the training set as an output of the neural network. Initial values of weights inside the neural network may be random, and the pre-trained neural network is obtained, so that the output of the neural network is consistent with the training set.

Figure 9:
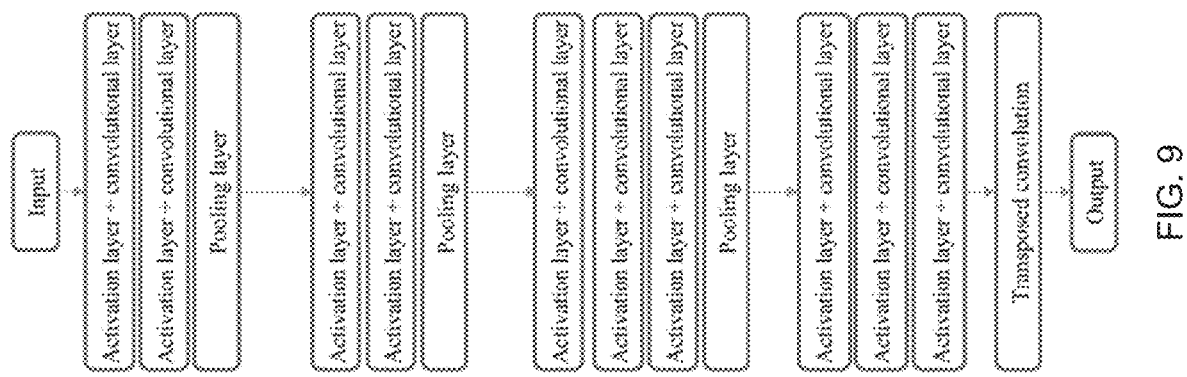
FIG. 9 is a modular block diagram of a neural network according to an embodiment of the present invention.

FIG. 9 is a modular diagram of a neural network according to an embodiment of the present invention. The neural network of the present invention employs a convolutional neural network including a convolutional layer, an activation layer, a pooling layer, and a transposed convolutional layer. By setting initial parameters and a loss function, a model of the convolutional neural network is trained using the identified training set, to obtain the trained convolutional neural network model.

Specifically, the pre-training process of the neural network according to an embodiment of the present invention is as follows: parameters of a convolutional neural network are randomly initialized, detailed features of a region of interest of the image are recognized by the convolutional layer and the activation layer, the image size is reduced by the pooling layer, features are then extracted by the convolutional layer and the activation layer, and finally transposed convolution is performed to map the features to a high-dimensional space. By defining the loss function, the randomly initialized internal weights are updated to generate the pre-trained neural network model. A newly captured pre-scan image is input to the pre-trained neural network model, the neural network model will find the maximum values of pixel positions pixel by pixel as classification of the pixels, and then output an image having the same resolution as the input pixels and having the identified region of interest.

In some embodiments, the internal weights of the neural network are not initialized randomly, but are based on other preset values, such as internal weights of neural networks that are sensitive to some image features in other applications. The randomly initialized convolutional neural network will take a long time or even difficult to converge, the method of transplanting the initial weights of the existing neural network can effectively reduce the pre-training time and improve the pre-training efficiency in the case where the training image set data of pre-scan images is small, so that the pre-training of the neural network can achieve the same convergence effect and locally optimum effect as actual training using massive images.

Preferably, a Vgg full convolutional neural network has high sensitivity to the shape of images. In an embodiment, parameters of first three layers of the Vgg full convolutional neural network are transplanted as the initial weights of this neural network. It should be noted that in other embodiments, some or all parameters of different types of existing convolutional neural networks may be transplanted according to different application requirements, including but not limited to a Vgg full convolutional neural network, a U-net, and other convolutional neural networks.

Further, the pre-scan image is pre-processed before entering the convolutional neural network, and the pre-scan image is mapped into a red, green, and blue (RGB) three-color domain to obtain a pre-scan image in a red, green, and blue (RGB) format. In an embodiment, the size of the pre-scan image may be arbitrary, and the entire pre-scan image is traversed using a window of 224*224 at a step size of 50 to obtain a subset of the pre-scan image. Such an operation can increase the number of samples while avoiding overfitting. Each image in the subset is converted to a pre-scan image in the red, green, and blue (RGB) format, that is, the pre-scan image is three image sets in a red, green, and blue (RGB) color gamut. Afterwards, the pre-scan image is used as an input to train a part of parameters of the Vgg full convolutional neural network. Such pre-processing operations improve the compatibility with the full convolutional neural network on one hand, and on the other hand, as feature recognition is performed on all of three dimensions including red, green, and blue, the accuracy and robustness of the recognition are improved, and the accuracy can reach more than 95%.

The pre-training process described above can be used to train the neural network by R&D personnel during the development stage of the device. Various parameters of the pre-trained neural network are solidified in a readable storage medium of the medical device. Preferably, in some embodiments, a self-learning neural network is selected, acquisition software at a user terminal is used, and images of some organs of regions of interest manually selected by the physician are used as an output, to continue training the neural network. In this way, the weights of the neural network can be further optimized during use, and the accuracy of recognition is improved, thus improving the efficiency of the medical device.

Some exemplary embodiments have been described above; however, it should be understood that various modifications may be made. For example, if the described techniques are performed in a different order and/or if the components of the described system, architecture, device, or circuit are combined in other manners and/or replaced or supplemented with additional components or equivalents thereof, suitable results can be achieved. Accordingly, other implementations also fall within the protection scope of the claims.

The invention claimed is:

1. A computer aided scanning method for a medical device, comprising:
   recognizing and analyzing a pre-scan image through a pre-trained neural network to determine and identify a region of interest in the pre-scan image;
   determining, according to feature information of the identified region of interest, scanning parameters for further scanning of the region of interest; and
   determining a feature point in the identified region of interest, and determining the auxiliary line based on at least two of the feature points;
   wherein the scanning parameters for further scanning of the region of interest are determined by determining an auxiliary line in the pre-scan image;
   wherein the feature point comprises a geometric center point of the identified region of interest, and the auxiliary line is determined by drawing a perpendicular line based on two adjacent geometric center points.

2. The computer aided scanning method for a medical device of claim 1, wherein theneural network is trained by the following steps:
   capturing a plurality of pre-scan images to obtain a pre-scan image set;
   marking regions of interest on the pre-scan images to obtain a training set; and
   training a neural network by using the pre-scan image set as an input and the training setas an output to obtain the pre-trained neural network.

3. The computer aided scanning method for a medical device of claim 1, wherein the method further comprises: converting the pre-scan image acquired when pre-scanningof the medical device is performed into a pre-scan image in a red, green, and blue (RGB) format, and the pre-trained neural network recognizes and analyzes the pre-scan image in the red, green, and blue (RGB) format, and outputs a binary image having the identified region of interest.

4. The computer aided scanning method for a medical device of claim 1, wherein the featurepoint comprises a vertex of the identified region of interest, and the auxiliary line is determined by fitting a straight line based on two adjacent groups of vertexes.

5. A medical device, comprising:
a scanning portion, configured to capture a pre-scan image; and
a computing portion, comprising:
a pre-trained neural network, wherein the pre-trained neural network is configured to recognize and analyze the pre-scan image to determine and identify a region of interest in thepre-scan image; and
the computing portion is configured to determine, according to feature information of the identified region of interest, scanning parameters for further scanning of the region of interest;
wherein the computing portion is configured to determine the scanning parameters for further scanning of the region of interest by determining an auxiliary line in the pre-scan image;
wherein the computing portion is configured to determine a feature point in the identified region of interest, and determine the auxiliary line based on at least two of the feature points; and
wherein the computing portion is configured to determine a geometric center point of the identified region of interest as the feature point, and determine the auxiliary line by drawing a perpendicular line based on two adjacent geometric center points.

6. The medical device of claim 5, wherein the computing portion further comprises a pre-processing portion, configured to convert the pre-scan image acquired when pre-scanning of the medical device is performed into a pre-scan image in a red, green, and blue (RGB) format, and the pre-trained neural network recognizes and analyzes the pre-scan image in the red, green, andblue (RGB) format, and outputs a binary image having the identified region of interest.

7. The medical device of claim 5, wherein the computing portion is configured to determine a vertex of the identified region of interest, and determine the auxiliary line by fittinga straight line based on two adjacent groups of vertexes.

* * * * *